US 6,710,049 B2

(12) United States Patent
Salman et al.

(10) Patent No.: US 6,710,049 B2
(45) Date of Patent: Mar. 23, 2004

(54) AZOLE COMPOUNDS AS ANTI-FUNGAL AGENTS

(75) Inventors: Mohammed Salman, Haryana (IN); Rita Katoch, Chandigarh (IN); Ashwani Kumar Verma, New Delhi (IN); Jitendra Sattigeri, Haryana (IN); Ashok Rattan, New Delhi (IN)

(73) Assignee: Ranbaxy Laboratories Limited, New Delhi (IN)

( * ) Notice: Subject to any disclaimer, the term of this patent is extended or adjusted under 35 U.S.C. 154(b) by 33 days.

(21) Appl. No.: 10/026,235

(22) Filed: Dec. 21, 2001

(65) Prior Publication Data

US 2002/0119984 A1 Aug. 29, 2002

(30) Foreign Application Priority Data

Dec. 26, 2000 (IN) .................................. 1197/DEL/2000

(51) Int. Cl.[7] .................. A61K 31/496; A61K 31/4196; C07D 403/08; C07D 403/12; C07D 403/14
(52) U.S. Cl. .................. 514/254.05; 514/384; 544/366; 548/263.4; 548/263.8; 548/264.6
(58) Field of Search ....................... 544/366; 548/264.6, 548/263.4, 263.8; 514/254.05, 384

(56) References Cited

U.S. PATENT DOCUMENTS

| 5,371,101 A | 12/1994 | Itoh et al. .................... 514/383 |
| 5,677,464 A | 10/1997 | Itoh et al. ................. 548/246.6 |
| 6,034,248 A | 3/2000 | Itoh et al. .................... 548/235 |
| 6,166,059 A | * 12/2000 | Jautelat et al. |

FOREIGN PATENT DOCUMENTS

| EP | 0 659 751 | 6/1995 |
| GB | 0 567 981 B1 | 7/1998 |
| WO | WO 01/66551 | 9/2001 |

OTHER PUBLICATIONS

Itoh, K. et al., "TAK–187, A New Antifungal Triazole: Synthesis and Antifungal Activity," *Abstracts of the 36th ICAAC, Monday Session 49*, Abstract F74, (Sep. 15–18, 1996).

Pfaller, M.A. et al., "Antifungal Activity of a New Triazole, SCH 56592, Compared with Four Other Antifungal Agents Tested Against Clinical Isolates," *Abstracts of the 36th ICAAC, Monday Session 50*, Abstract F87, (Sep. 15–18, 1996).

Urbina, J.A., et al., "In vitro and in vivo antiproliferative effects of SCH 56592 agents *Trypanosoma cruzi*, the causative agent of Chagas disease," *Abstracts of the 36th ICAAC, Monday Session 50*, Abstract F102, (Sep. 15–18, 1996).

Kitazaki, T. et al., "TAK–456 and the Water–Soluble Prodrug TAK–457, New Antifungal Triazoles: Synthesis and In Vitro Antifungal Activity," *40th ICAAC Abstracts, Monday Session 111 (F,J)*, Abstract 1085, (Sep. 17–20, 2000).

Iizawa, Y. et al., "TAK–456 and the Water–Soluble Prodrug TAK–457, New Antifungal Triazoles: In Vitro and In Vivo Antifungal Activity," *40th ICAAC Abstracts, Monday Session 111 (F,J)*, Abstract 1086, (Sep. 17–20, 2000).

Naito, T. et al., "ER–30346: Triazole Antifungal," *Drugs of the Future*, 21 (1), pp. 20–24 (1996).

Yokoyama, et al., "Improved O/S Exchange Agents," *Communications*, pp. 827–829 (Oct. 1984).

* cited by examiner

*Primary Examiner*—Emily Bernhardt
(74) *Attorney, Agent, or Firm*—Jayadeep R. Deshmukh, Esq.; George E. Heibel, Esq.

(57) ABSTRACT

The present invention relates to the derivatives of specially substituted azole compounds which have improved antifungal activity as compared with presently available agents in this class and the processes for the preparation thereof. This invention also relates to pharmaceutical preparations containing the compounds of the present invention and their use in treating and/or preventing the fungal infections in mammals, preferably humans.

10 Claims, No Drawings

AZOLE COMPOUNDS AS ANTI-FUNGAL AGENTS

FIELD OF THE INVENTION

The present invention relates to the derivatives of specially substituted azole compounds which have improved antifungal activity as compared with presently available agents in this class and the processes for the preparation thereof. This invention also relates to pharmaceutical preparations containing the compounds of the present invention and their use in treating and/or preventing the fungal infections in mammals, preferably humans.

BACKGROUND OF THE INVENTION

Life threatening, systemic fungal infections continue to be a significant problem in health care today. In particular, patients who become "immunocompromised" as a result of diabetes, cancer, prolonged steroid therapy, organ transplantation anti-rejection therapy, the acquired immune deficiency syndrome (AIDS) or other physiologically or immunologically comprising syndromes, are especially susceptible to opportunistic fungal infections.

Since the 1950s and 1960s and until recently, the key opportunistic fungal pathogens with which clinicians had to contend were *Candida albicans, Asperigillus fumigatus*, and the zygomiycetes, which cause mucormycosis, a rapidly fatal infection especially in diabetic patients. Today, non-albicans Candida have become more frequent, as have other Aspergillus species. Candida species are now the fourth most common cause of nosocomial blood stream infection and they are associated with an extremely high mortality rate of 40%. From 1980 to 1990, the incidence of fungal infections in the US hospitals nearly doubled, from 2.0 to 3.8% of patients discharged. The most marked increase in fungal infection rates occurred not only in transplant units or oncology centers, but also in surgical services. These changing patterns demonstrate that fungal infections are no longer limited to the most severly immunosuppressed patients.

During the past two decades, a substantial shift in the epidemiology of candidemia due to different Candida species has occurred. In the 1960s and 1970s, *Candida albicans* accounted for 85–90% of cases of candidemia. In 1999, however, only 42% of candidemia cases were caused by *C. alibicans*, while non-albicans candida accounted for the remainder.

Cryptococosis is a leading cause of morbidity among AIDS patients. The incidence of life threatening cryptococcal infection among these patients have been estimated to vary from 10 to 30%. During initial therapy, 10–20% of these patients die and 30 to 60% patients succumb within a year. *Penicillinium marneffei* has been frequently isolated from HIV+ patients, especially in Southeast Asia.

The most common causative agent of mucormycosis is rhizopus, a common bread mould that lives on any organic material. Other pathogens include Mucor, Rhizomucor and Absidia. Zygomycetes include twenty different fungi, all appearing the same histologically. The severely immunocompromised patient may become infected with zygomycetes via respiratory inhalation.

Fusarium is the most prevalent plant fungus worldwide, and it is now recognized as human pathogen as well. Fusarium infections can occur in immunocompetent or immuno suppressed individuals. Fusarium infection is life-threatening and associated with a poor prognosis.

*Penicillium marneffei* is an environmental fungi that can cause serious, life-threatening infections in immunosuppressed patients. *Penicillium marneffei* has gained particular attention during the AIDS pandemic, as it may produce disease that is clinically indistinugishable from disseminated histoplasmosis.

Invasive aspergillosis has also become a leading cause of death, mainly among patients suffering from acute leukaemia or after allogenic bone marrow transfusion and after cytotoxic treatment of these conditions. It also occurs in patients with condition such as AIDS and chronic granulomatous disease. At present, only Amphotericin B and itraconazole are available for treatment of aspergillosis. Inspite of their activity in-vitro, the effect of these drugs in-vivo against *Aspergillus fumigatus* remains low and as a consequence mortality from invasive aspergillosis remains high.

Over the last three decades important progress has been made in the therapy of systematic fungal infections. Although chemotherapeutic agents such as flucytosine and potassium iodide are effective against selected fungal diseases, the primary drugs used to treat systemic mycoses are amphotericin B and the azole compounds. Despite the general effectiveness of amphotericin B, it is associated with a number of complications and unique toxicities that limit its use. Furthermore, the drug is poorly absorbed from the gastrointestinal tract necessitating intravenous administration. In addition, amphotericin B penetrates poorly into cerebrospinal fluid (CSF) of both normal and inflamed meninges.

The problems associated with amphotericin B have stimulated search for new agents. Within the available drugs to treat fungal infections, the azole class appears to be most promising. This class of compounds inhibits the biosynthesis of ergosterol in fungi, which is the main constituent of fungal cell membrane. Of the various representative antifungals, early azoles used were clotrimazole, miconazole, and tioconazole, which were potent against a wide range of fungi pathogenic to human. Clortrimazole was the first oral azole proven to be effective in experimental and human mycosis. However, brief courses of treatment with clotrimazole lead to the induction of liver microsomal enzymes which in turn increase the metabolism of the drug, thereby diminishing its antifungal activity. In contrast, miconazole, which became available around the same time as clotrimazole, is not rapidly metabolized and is an effective intravenous therapy for many systemic fungal diseases. Unfortunately, the use of miconazole is limited by its multiple toxic effects.

The in-vitro activity of clotrimazole, miconazole and tioconazole was not well exhibited in in-vivo models due to poor oral bioavailability and metabolic vulnerability. Ketoconazole was the first drug that could be used against systemic fungal infection and successfully delivered through oral route. However, it was still quite susceptible to metabolic inactivation and also caused impotence and gynacomastia probably due to its activity against human cytochrome P450 enzymes.

Even with the advent of ketoconazole, the search for improved antifungal azole agents has continued due in part to concerns over the potential for toxicity and poor penetration into cerebrospinal fluid (CSF) associated with ketoconazole. Several azoles have been developed as topical agents primarily directed at superficial candidal and dermatophytic infections.

Fluconazole is the current drug of choice for treatment of severe infections caused by Candida species and *C.neofor-*

*mans*. However, fluconazole has only weak activity against isolates of Aspergillus species [minimum inhibitory concentration (MIC) values of 400 µg/ml], since the drug has low potency ($IC_{50}$=4.8 µM) against lanosterol 14α-demethylase, the target enzyme in the fungus. Itraconazole, another triazole antifungal compound, generally is more active than fluconazole in the treatment of aspergillosis, but its activity in the clinic remains mixed as it showed variable oral availability, low solubility and very high protein binding besides causing ovarian cancer in animals.

The development of the earlier compounds which included SCH 39304 (Genoconazole), SCH 42427 (Saperaconazole) and BAY R 8783 (Electrazole) had to be discontinued as a result of safety concerns. Another promising triazole, D0870, a derivative of fluconazole, exhibited significant variations in plasma pharmacokinetics besides having weak anti-Aspergillus activity. Other fluconazole derivatives in different stages of development include Voriconazole and ER 30346 (BMS 207147). Voriconazole also shows non-linear pharmacokinetics besides some concern regarding its ocular toxicity. ER 30346's anti-aspergillus activity, both in-vitro and in-vivo, is at best, only equal to itraconazole's activity. SCH 56592 is a hydroxylated analogue of itraconazole with potent in-vitro and in-vivo activity, but is undetectable in CSF even when the serum drug concentration after several days of treatment are 25 to 100 times above the MIC for the most resistant *C. neoformans*. Thus, the potent activity of SCH 56592 for *C. neoformans* is partially negated by its low concentration at the site of infection in the central nervous system. The above candidates of azoles are discussed in the following publications:

SCH 56592; *Antimicrobial agents and chemotherapy*, 40, 1910 (1996); 36$^{th}$ Interscience Confernece on Antimicrobial agents and chemotherapy, September, 1996, New Orleans, Abst. To F-87-F-102.

TAK-187; 36$^{th}$ Interscience Conference *Antimicrobial agents and Chemotherapy*, September, 1996, New Orleans, Abst. F 74; EP 567892.

TAK-456 and TAK-457; 40$^{th}$ Interscience Conference on *Antimicrobial agents and chemotherapy*, Toronto, Canada, Abs. No. 1085 and 1086; U.S. Pat. No. 6,034, 248.

ER-30346: *Drugs of the Future*, 21, 20 (1996).

Various derivatives of azole compounds have been covered in U.S. Pat. No. 5,371,101 assigned to Takeda. But none of them satisfies the medical needs completely, as they offer a limited spectrum of activity and low potency.

Thus, the antifungals available in the market suffer with drawbacks such as toxicity, narrow spectrum of activity and fungistatic profile rather fungicidal. Some of them also exhibit drug-drug interactions and, as a result, therapy becomes complex. In view of the high incidence of fungal infections in immunocompromised patients and the recent trends for the steady increase of the population of such patients, demands for new antifungal agents with broad spectrum of activity and good pharamcokinetic properties has increased. The continuing demand for safe and effective broad spectrum antifungal agent with favourable pharmacokinetic properties has spurred both the design and development of new systemically active antifungal triazoles.

Despite the therapeutic success of fluconazole and itraconazole, there remains a significant need for improved, broad spectrum, fungicidal rather than fungistatic, better tolerated, less toxic, safe at efficacious doses and more potent antifungal compounds with minimal potential for development of resistance among target fungi. Therefore, development of antifungal agents is still a big challenge.

SUMMARY OF THE INVENTION

The present invention relates to new substituted azole compounds which can be utilized to treat and/or prevent the fungal infections in mammals, preferably in humans.

The first aspect of the present invention provides compounds of Formula I, and its pharmaceutically acceptable salts, enantiomers, diastereomers, N-oxides, prodrugs or metabolities,

FORMULA-I

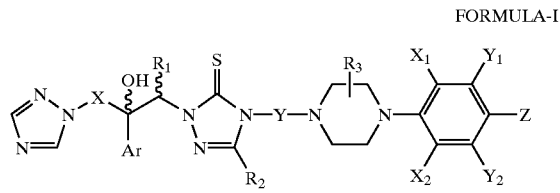

wherein X is selected from the group consisting of $CH_2$, CO, CS and $SO_2$;

Ar is a substituted phenyl group having one to three substituents independently selected from a halogen (e.g., fluorine, chlorine, bromine, or iodine), $C_1$–$C_4$ alkyl, halogenated lower ($C_1$–$C_4$) alkyl group and halogenated lower ($C_1$–$C_4$) alkoxy group such as 2,4-difluorophenyl, 2,4-dichlorophenyl, 4-chlorpheny), 4-fluorophenyl, 2-chlorophenyl, 2-fluorophenyl, 4-trifluoromethylphenyl, 2-fluoro-4-chlorophenyl, 2-chloro-4-fluorophenyl, 4-trifluoromethoxyphenyl, 2,4,6-trifluorophenyl, 4-bromophenyl;

$R_1$ and $R_2$ are each independently selected from the group consisting of hydrogen, $C_1$–$C_4$ alkyl, $C_1$–$C_4$ alkoxy, amino, hydroxy, nitro, cyano, carboxyl, protected carboxyl, and $SO_2R'$ wherein R' is hydrogen, alkyl or aryl;

Y is a phenyl group which is unsubstituted or substituted by 1–3 substituents each independently selected from the group consisting of halogen, nitro, amino, cyano, carboxyl, protected carboxyl, hydroxy, $C_1$–$C_4$ alkyl, $C_1$–$C_4$ alkoxy and $SO_2R'$ wherein R' is hydrogen, alkyl or aryl;

$R_3$ is selected from the group consisting of hydrogen, $C_1$–$C_4$ alkyl group, $C_1$–$C_4$ alkoxy, nitro, amino, cyano, carboxyl, protected caboxyl and $SO_2R'$ wherein R' is hydrogen, alkyl or aryl, and $X_1$, $X_2$, $Y_1$, $Y_2$ and Z are independently selected from the group consisting of hydrogen halogen, nitro, cyano, amino, sulphonyl, aryl, $C_1$–$C_4$, alkyl, $C_1$–$C_4$ alkoxy, halogenated lower ($C_1$–$C_4$) alkyl group, halogenated lower ($C_1$–$C_4$) alkoxy group and carboxyl, or protected carboxyl.

When $R_1$ is other than hydrogen, Formula I has two asymmetric centers and there are four possible enantiomers i.e. RR, RS, SR and SS. This invention relates to the mixture of enantiomers as well as individual isomers and the most preferred isomer in this situation is RR.

According to the second aspect of the invention, there are provided compounds of Formula II, and its pharmaceutically acceptable salts, enantiomers, diastereomers, N-oxides, prodrugs or metabolities,

FORMULA-II

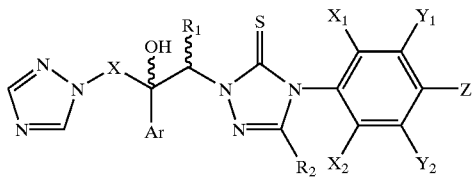

wherein X, Ar, $R_1$, $R_2$, $X_1$, $X_2$, $Y_1$, $Y_2$ and Z are the same as defined earlier.

When $R_1$ is other than hydrogen, Formula II has two asymmetric centres and there are four possible enantiomers i.e. RR, RS, SR and SS. This invention relates to the mixture of enantiomers as well as individual isomers and the most preferred isomer in this situation is RR.

It has now been found that the compound namely, 2-{[1R,2R]-2-(2,4-difluorophenyl)-2-hydroxy-1-methyl-3-(1H-1,2,4-triazol-1-yl)propyl}-4-(2',2',3',3'-tetrafluoropropoxyphenyl)-3-(2H,4H)-1,2,4-thiotriazolone has unexpectedly potent activity against clinically important filamentous species of fungi, besides increased spectrum. The compound is shown to be fungicidal against some filamentous fungi.

Pharmaceutically acceptable, non-toxic acid addition salts of the compounds of the present invention of Formulae I and II, may be formed with inorganic or organic acids, by methods well known in the art.

It is also an object of the invention to provide a method for synthesis of the novel compounds.

It is further object of the present invention to provide compositions containing the novel compounds of the present invention in the treatment of fungal infections.

The present invention also includes within its scope prodrugs of the compounds of Formulae I and II. In general, such prodrugs will be functional derivatives of these compounds which readily get converted in-vivo into defined compounds. Conventional procedures for the selection and preparation of suitable prodrugs are known.

The invention also includes pharmaceutically acceptable salts, enantiomers, diastereomers, N-oxides, prodrugs, metabolites in combination with pharmaceutically acceptable carriers and optional excipients.

Other advantages of the invention will be set forth in the description which follows, and in part will be apparent from the description, or may be learned by the practice of the invention.

DETAILED DESCRIPTION OF THE INVENTION

In order to achieve the above mentioned aspects and in accordance with the purpose of the invention as embodied and described herein, there are provided processes for the synthesis of compounds of Formulae I and II, wherein X, Ar, $R_1$, $R_2$, $R_3$, Y, $X_1$, $X_2$, $Y_1$, $Y_2$ and Z are the same and defined earlier. The starting compounds of Formulae III and IV are known from our published PCT application WO 01/66551 and U.S. Pat. No. 5,371,101, respectively and are incorporated herein by reference.

SCHEME I

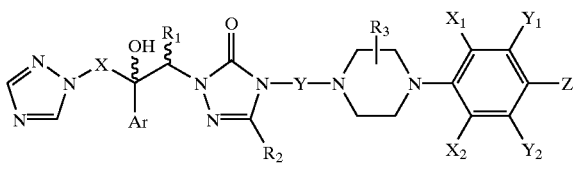

FORMULA-III

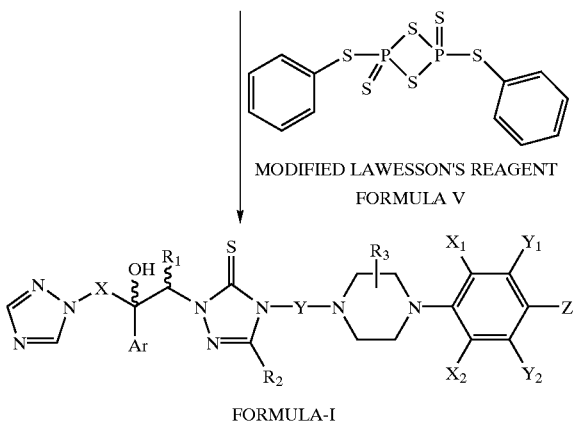

MODIFIED LAWESSON'S REAGENT
FORMULA V

FORMULA-I

In Scheme I there is provided a process for preparing a compound of Formula I, as shown above and its pharmaceutically acceptable salts, enantiomers, diastereomers, N-oxides, prodrugs, or metabolites, wherein X is selected from the group consisting of $CH_2$, CO, CS and $SO_2$;

Ar is a substituted phenyl group having one to three substituents independently selected from a halogen (e.g., fluorine, chlorine, bromine, or iodine) $C_1$–$C_4$ alkyl, halogenated lower ($C_1$–$C_4$) alkyl group and halogenated lower ($C_1$–$C_4$) alkoxy group such as 2,4-difluorophenyl, 2,4-dichlorophenyl, 4-chlorophenyl, 4-fluorophenyl, 2-chlorophenyl, 2-fluorophenyl, 4-trifluoromethylphenyl, 2-fluoro-4-chlorophenyl, 2-chloro-4-fluorophenyl, 4-trifluoromethoxyphenyl, 2,4,6-trifluorophenyl, 4-bromophenyl;

$R_1$ and $R_2$ are each independently selected from the group consisting of hydrogen, $C_1$–$C_4$ alkyl, $C_1$–$C_4$ alkoxy, amino, hydroxy, nitro, cyano, carboxyl, protected carboxyl, and $SO_2R'$ wherein R' is hydrogen, alkyl or aryl;

Y is a phenyl group which is unsubstituted or substituted by 1–3 substituents each independently selected from the group consisting of halogen, nitro, amino, cyano, carboxyl, protected carboxyl, hydroxy, $C_1$–$C_4$ alkyl, $C_1$–$C_4$ alkoxy and $SO_2R'$ wherein R' is hydrogen, alkyl or aryl;

$R_3$ is selected from the group consisting of hydrogen, $C_1$–$C_4$ alkyl group, $C_1$–$C_4$ alkoxy, nitro, amino, cyano, carboxyl, protected caboxyl and $SO_2R'$ wherein R' is hydrogen, alkyl or aryl, and $X_1$, $X_2$, $Y_1$, $Y_2$ and Z are independently selected from the group consisting of hydrogen, halogen, nitro, cyano, amino, sulphonyl, aryl, $C_1$–$C_4$ alkyl, $C_1$–$C_4$ alkoxy, halogenated lower ($C_1$–$C_4$) alkyl group, halogenated lower ($C_1$–$C_4$) alkoxy group and carboxyl, or protected carboxyl.

When $R_1$ is other than hydrogen, Formula I has two asymmetric centers and there are four possible enantiomers i.e. RR, RS, SR and SS. This invention relates to the mixture of enantiomers as well as individual isomers and the most preferred isomer in this situation is RR;

which comprises reacting the appropriate oxo compound of Formula III, wherein X, Ar, $R_1$, $R_2$, Y, $R_3$, $X_1$, $X_2$, $Y_1$, $Y_2$ and Z have the same meanings as defined above, with modified Lawesson's reagent of Formula V, to afford the desired compound of Formula I. The oxo compound of Formula III may be prepared according to the procedure as disclosed in our published PCT application WO 01/66551. The modified Lawesson's reagent is prepared according to the procedure as disclosed by Masataka Yokohamna et al. in *Synthesis*, pp 827–829 (1984).

SCHEME II

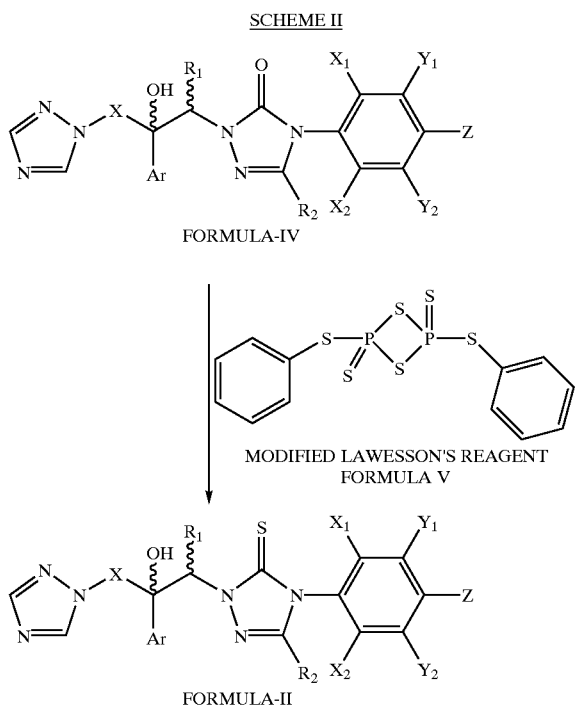

MODIFIED LAWESSON'S REAGENT
FORMULA V

FORMULA-II

In Scheme II there is provided a process for preparing a compound of Formula II, as shown above and its pharmaceutically acceptable salts, enantiomers, diastereomers N-oxides, prodrugs or metabolities, wherein X is selected from the group consisting of $CH_2$, CO, CS and $SO_2$;

Ar is a substituted phenyl group having one to three substituents independently selected from a halogen (e.g., fluorine, chlorine, bromine, or iodine), $C_1$–$C_4$ alkyl, halogenated lower ($C_1$–$C_4$) alkyl group and halogenated lower ($C_1$–$C_4$) alkoxy group such as 2,4-difluorophenyl, 2,4-dichlorophenyl, 4-chlorophenyl, 4-fluorophenyl, 2-chlorophenyl, 2-fluorophenyl, 4-trifluoromethylphenyl, 2-fluoro-4-chlorophenyl, 2-chloro-4-fluorophenyl, 4-trifluoromethoxyphenyl, 2,4,6-trifluorophenyl, 4-bromophenyl;

$R_1$ and $R_2$ are each independently selected from the group consisting of hydrogen, $C_1$–$C_4$ alkyl, $C_1$–$C_4$ alkoxy, amino, hydroxy, nitro, cyano, carboxyl, protected carboxyl, and $SO_2R'$ wherein R' is hydrogen, alkyl or aryl; and $X_1$, $X_2$, $Y_1$, $Y_2$ and Z are independently selected from the group consisting of hydrogen, halogen, nitro, cyano, amino, sulphonyl, aryl, $C_1$–$C_4$, alkyl, $C_1$–$C_4$ alkoxy, halogenated lower ($C_1$–$C_4$) alkyl group, halogenated lower ($C_1$–$C_4$) alkoxy group and carboxyl, or protected carboxyl.

When $R_1$ is other than hydrogen, Formula II has two asymmetric centers and ther are four possible enantiomers i.e. RR, RS, SR and SS. This invention relates to the mixture of enantiomers as well as individual isomers and the most preferred isomer in this situation is RR; which comprises reacting the oxo compound of Formula IV, wherein X, Ar, $R_1$, $R_2$, $X_1$, $X_2$, $Y_1$, $Y_2$ and Z have the same meanings as defined above, with modified Lawesson's reagents [prepared according to the procedure as disclosed by Masataka Yokohama et al in *Synthesis*, pp 827–829 (1984)] of Formula V, to afford the desired compound of Formula II. The starting compound of Formula IV is prepared by following the procedure as disclosed in the U.S. Pat. No. 5,371,101.

In the above schemes where specific solvent and specific modified Lawesson's reagent are mentioned, it is to be understood that other solvents and Lawesson's reagent or modification thereof may be used. Similarly, the reaction temperature and duration of the reaction may be adjusted according to the need. An illustrative list of some of the compounds according to the invention and capable of being produced by Schemes I and II include:

Compound No. 1: 2-{[1R2R]-2-(2,4-Difluorophenyl)-2-hydroxy-1-methyl-3-(1H-1,2,4-triazole-1-yl)propyl}-4-{4-[4-(4-chlorophenyl)-1-piperizinyl]phenyl}-3-(2H,4H)-1,2,4-thiotriazolone Compound No. 2: 2-{[1R2R]-2-(2,4-Difluorophenyl)-2-hydroxy-1-methyl-3-(1H-1,2,4-triazole-1-yl)propyl}-1-[4-(4-methoxyphenyl)-3-(2H,4H)-1,2,4-thiotriazolone Compound No. 3: 2-{[1R,2R]-2-(2,4-difluorophenyl)-2-hydroxy-1-methyl-3-(1H-1,2,4-triazol-1-yl)propyl}-4-(2',2',3',3'-tetrafluoropropoxyphenyl(-3-(2H,4H)-1,2,4-thiotriazolone The examples mentioned below demonstrate the general synthetic procedure as well as specific preparation for the preferred compound. The examples are given to illustrate the details of the invention and should not be constrained to limit the scope of the present invention.

The compounds were characterized using NMR, IR and were purified by chromatography. Crude products were subjected to column chromatographic purification using silica gel (100–200 or 60–120 mesh) as stationary phase.

EXAMPLE 1

Typical Procedure for the Preparation of Compounds of Formula I

A mixture of the appropriate oxo compound (1.15 mmol) and modified Lawesson's reagent (6.34 mmol) in toluene (140 mL) was heated at 120° C. (bath temperature) for 3.5 hours. The reaction mixture was then cooled to room temperature, and the solvent was removed in vacuo. The residue thus obtained was washed several times with dichloromethane. The dichloromethane soluble fractions were combined and concentrated in vacuo. Purification by column chromatography (100–200 mesh silica gel, 10–15% ethyl acetate/dichloromethane) afforded the desired sulfur analog in 44.5% yield and ~90% HPLC purity. Re-crystallization with absolute ethanol afforded the pure compound in about 98% purity (by HPLC).

EXAMPLE 2

Typical Procedure for the Preparation of Compounds of Formula II

The oxo compound (1 mol) and Lawesson's Reagent (2 mol equivalent.) were dried under high vacuum for 10 min, flushed with nitrogen and heated to reflux in toluene for 15 hours. Reaction mixture was concentrated to dryness, re-dissolved in dichloromethane and purified by column chromatography (silica gel, 100–200 mesh), using dichloromethane-ethyl acetate mixtures (9.5:0.5 to 6:4) to afford the desired product in about 10% yield.

EXAMPLE 3

Preparation of 2-{[1R,2R]-2-(2,4-difluorophenyl)-2-hydroxy-1-methyl-3-(1H-1,2,4-triazol-1-yl)propyl}-4-(2',2',3',3'-tetrafluoropropoxyphenyl)-3-(2H,4H)-1,2,4-thiotriazolone A mixture of 2-{[1R,2R]-2-(2,4-difluorophenyl)-2-hydroxy-1-methyl-3-(1H-1,2,4-triazol-1-yl)propyl}-4-(2',2',3',3'-tetrafluoropropoxyphenyl)-3-(2H,4H)-1,2,4-thiotriazolone (1.41 g) and Lawesson's Reagent (2.08 g, 2.0 m eq) was heated to reflux in toluene for 3–15 hr.

Reaction mixture was concentrated under vacuum to give yellow semi-solid which was stirred with dichloromethane for 10 min. The solid was filtered and washed with dichloromethane. The combined filtrate and washings were concentrated under vacuum to give yellow semi-solid which was purified using column chromatography (first using silica gel, 60–120 mesh and then active alumina, basic) to give white fluffy solid as a desired compound (0.3 g).

Assignment of RR/SS was done on the basis of $^1$HNMR analysis.

An illustrative list of some of the compounds of the invention which were synthesised by one or more of the above described methods is given below along with their $^1$HNMR data. All $^1$HNMR spectra were recorded on Brucker AMX 300 NMR machines (300 MHZ) using CDCl$_3$ as a solvent and TMS as an internal standard unless otherwise specified. All values are given in ppm.

Symbols in the examples have the meanings; s:singlet; d: doublet; t: triplet; q: quartet; dd: double doublet; m:multiplet; br:broad; J:coupling constant:

Compound No. 1: 2-{[1R,2R]-2-(2,4-Difluorophenyl)-2-hydroxy-1-methyl-3-(1H-1,2,4-triazole-1-yl)propyl}-4-{4-[4-(4-chlorophenyl)-1-piperizinyl]phenyl}-3-(2H,4H)-1,2,4-thiotriazolone

| | |
|---|---|
| m.p.: | 129–130° C. |
| IR (KBr): | 3421, 2916, 2847, 1614, 1595 cm$^{-1}$ |
| NMR (CDCl$_3$): | δ1.33(d, J=6.7Hz, CH—CH$_3$), 3.33–3.42(m, 8H, piperazine-H), 4.35(d, J=14.3Hz, 1H, CH$_2$-Triazole), 5.14(d, J=14.4Hz, CH$_2$-Triazole), 5.19(bs, 1H, —OH), 5.93(q, J=6.7Hz, 1H, CH—CH$_3$), 6.81–6.90(m, 4H, Ar—H), 7.05(d, J=8.6Hz, 2H, Ar—H), 7.24(d, J=8.5Hz, 2H, Ar—H), 7.43(d, J=8.5Hz, 2H, Ar—H), 7.60(m, 1H, 2,4-difluorophenyl-H), 7.74(s, 1H, thiotriazolone-H), 7.92(s, 1H, triazole-H), and 7.93(s, 1H, triazole-H). |
| Mass: | m/z 623.1 (M + 1) |

Compound No. 2: 2-{[1R,2R]-2-(2,4-Difluorophenyl)-2-hydroxy-1-methyl-3-(1H-1,2,4-triazole-1-yl)propyl}-1-[4-(4-methoxyphenyl)]-3-(2H,4H)-1,2,4-thiotriazolone

| | |
|---|---|
| m.p.: | 166–170° C. |
| IR (KBr): | 3436, 2924, 1615, 1511, 1476, 1258, 962 and 835 cm$^{-1}$ |
| NMR (CDCl$_3$): | δ1.36(d, 1H, J=9Hz; CH—CH$_3$), 3.873(s, 3H; OCH$_3$), 4.351(d, 1H, J=14.4Hz; triazole-CH$_2$), 5.703–5.202(m, 2H; triazole-CH$_2$ & OH), 5.933(q, 1H, J=6.9Hz, CH—CH$_3$), 6.81–6.87(m, 2H; Ar—H), 7.034–7.07(d, 2H; Ar—H), 7.455–7.483(d, 2H; Ar—H), 7.59–7.642(m, 1H; Ar—H), 7.31(s, 1H; Ar—H), and 7.927(s, 2H, Ar—H). |
| Mass: | m/z 459.0 (M + 1) |

Compound No. 3: 2-{[1R,2R]-2-(2,4-Difluorophenyl)-2-hydroxy-1-methyl-3-(1H-1,2,4-triazole-1-yl)propyl}-4-[(2',2',3',3'-tetrafluoropropoxyphenyl)-3-(2H,4H)-1,2,4-thiotriazolone

| | |
|---|---|
| m.p.: | 76.8–84.3° C. |
| IR (KBr): | 3447, 1618, 1515, 1423, 1135, 1110 and 867.6 cm$^{-1}$ |
| NMR (CDCl$_3$): | δ1.33(d, 3H, J=9Hz; CH—CH$_3$), 4.41(m, 3H; OCH$_2$CF$_2$ and triazole-CH$_2$), 5.16(d, 1H, J=14.4Hz; triazole-CH$_2$), 5.92(q, 1H, J=9Hz; CH—CH$_3$), 6.07(tt, 1H, J=53.4 and 4.5Hz; CF$_2$CF$_2$H), 6.85(m, 2H; Ar—H), 7.11(d, 2H; J= 9.0Hz; Ar—H), 7.58(m, 3H; Ar—H), 7.77(s, 1H), 7.96(s, 1H), and 8.26(s, 1H). |
| Mass: | m/z 559 (M + 1) |

Pharmacological Activity

Compounds of the Formulae I and II as shown herein, and their salts are useful in the curative or prophylactic treatment of fungal infections in animals, including humans. For example, they are useful in treating topical fungal infection in man caused by, among other organisms, species of Candida, Trichophyton, Microsporum or Epidermophyton in mucosal infections caused by *C. albicans* (eg. thrush and vaginal candidiasis). They can also be used in the treatment of systemic fungal infections caused by, for example, species of Candida (e. g. *Candida albicans*), *Cryptococcus neoformans, Aspergillus fumigatus*, Fusarium, Rhizopus or *Penicillinium marneffei*.

The compounds of the present invention have been found to have unexpectedly potent activity against clinically important filamentous species of fungi, besides increased spectrum. The compounds are fungicidal.

The in-vitro evaluation of the antifungal activity of the compounds can be performed by determining the minimum inhibitory concentration (MIC) as shown in Table 1 which is the concentration of the test compound in Rosewell Park Memorial Institute (RPMI) 1640 liquid medium buffered with 3-(Morpholino)propanesulphonic acid (MOPS) to pH 7, at which there is significant inhibition of the particular fungi. In practice the National Committee for Clinical Laboratory Standard (NCCLS) M27A document for Candida and Cryptococcus and M38P for Aspergillus was used to determine the MIC against yeast and filamentous fungi with suitable modifications for dermatophytes to other filamentous fungi. Three quality control strains were included each time the MIC were determined and readings recorded only when the Quality Control results fell into the acceptable range. After MIC results had been recorded, 100 μl from each of the well showing no growth was spread over Sabouraud Dextrose Agar (SDA) to determine the minimum fungicidal concentration (MFC) as shown in Table 2.

The in-vivo evaluation of the compound can be carried out at a series of dose levels by oral or I. V. injection to mice which are inoculated I.V. with the minimum lethal dose of *Candida albicans, Cryptococcus neoformans* or *Aspergillus fumigatus* by the tail vein. Activity is based on the survival of a treated group of mice after the death of an untreated group of mice. For Aspergillus and Cryptococcus infections, target organs were cultured after treatment to document the number of mice cured of the infection for further assessment of activity.

For human use, the antifungal compounds of the formula and their salts can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs, solutions or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

The solubility of a compound of the Formulae I and II in an aqueous medium may be improved by complexation with a hydroxyalkyl derivative of a cyclodextrin in the preparation of an appropriate pharmaceutical composition.

For oral and parenteral administration to human patients, the daily dosage level of the antifungal compounds of the Formulae I and II and their salts will be from 0.01 to 20 mg/kg (in single or divided doses) when administered by either the oral or parenteral routes. Thus tablets or capsules of the compound will contain from 5 mg to 0.5 gm of active compound for administration singly or two or more at a time, as appropriate. The physician in any event will determine the actual dosage which will be the most suitable for an individual patient and it will vary with age, weight and response of the particular patient. The above dosages are exemplary of the average case, there can, of course, be individual instances, where higher or lower dosage ranges are required and such are within the scope of this invention.

Alternatively, the antifungal compound of Formulae I and II can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin, or they can be incorporated, at a concentration between 1 and 10% into an ointment consisting of a white wax or white soft paraffin base together with such stabilizers and preservatives as may be required.

TABLE 1

Minimum Inhibitory Concentration (MIC) (μg/ml) of Standard drugs and compound of this invention against various fungi

|  | Fluconazole | Amphotericin-B | Itraconazole | Compound No.1 (This invention) | TAK 187 |
|---|---|---|---|---|---|
| 1. *C krusei* 6258 | 32 | 0.25 | 0.25 | 0.06 | 2 |
| 2. *C parapsilosis* 22019 | 2 | 0.25 | 0.03 | 0.004 | 0.03 |
| 3. *P variotii* 22319 | >128 | 0.03 | 0.016 | 0.004 | 0.25 |
| 4. *C albicans* A-26 | 0.5 | 0.25 | 0.016 | 0.016 | — |
| 5. *C albicans* Y01.19 | 8 | 0.125 | 0.25 | 0.03 | 2 |
| 6. *C glabrata* 90030 | 4 | 0.25 | 0.5 | 0.06 | 0.5 |
| 7. *C tropicalis* 750 | 0.5 | 0.25 | 0.016 | 0.008 | 0.125 |
| 8. *C krusei* 766.1 | 128 | 0.25 | 0.5 | 0.125 | 2 |
| 9. *C neoformans* M-106 | 4 | 0.03 | 0.03 | 0.008 | 0.06 |
| 10. *C neoformans* I | 1 | 0.06 | 0.03 | 0.008 | 0.03 |
| 11. *H capsulatum* | 4 | 0.125 | 0.03 | 0.06 | 0.25 |
| 12. *A fumigatus* I - 1011 | >128 | 0.25 | 0.06 | 0.016 | 4 |
| 13. *A fumigatus* II - 1012 | >128 | 0.125 | 0.06 | 0.008 | 8 |
| 14. *A fumigatus* J - 1032 | >128 | 0.25 | 0.03 | 0.008 | 4 |
| 15. *A fumigatus* K - 1033 | >128 | 0.125 | 0.06 | 0.008 | 8 |
| 16. *A fumigatus* L - 1034 | >128 | 0.25 | 0.06 | 0.008 | 4 |
| 17. *A fumigatus* SI-1 - 1019 | >128 | 0.5 | 0.03 | 0.016 | 2 |
| 18. *A fumigatus* 1008 | >128 | 0.25 | 0.06 | 0.016 | 4 |
| 19. *A fumigatus* PGI - 1023 | >128 | 0.125 | 0.03 | 0.016 | 8 |
| 20. *A flavus* P2 - 1045 | >128 | 1 | 0.06 | 0.016 | 4 |
| 21. *A flavus* P3 - 1041 | >128 | 0.5 | 0.06 | 0.008 | 8 |
| 22. *A flavus* E2 - 1043 | >128 | 1 | 0.03 | 0.008 | 4 |
| 23. *A flavus* E3 - 1044 | >128 | 1 | 0.03 | 0.016 | 1 |
| 24. *A flavus* E4 - 1042 | >128 | 0.125 | 0.06 | 0.008 | 4 |
| 25. *A niger* E5 - 1047 | >128 | 0.25 | 0.03 | 0.03 | 2 |
| 26. *A niger* P1 - 1046 | 128 | 0.25 | 0.125 | 0.03 | 0.5 |
| 27. Penicillium H - 1048 | >128 | 0.25 | 16 | 0.03 | 16 |
| 28. Penicillium I - 1049 | >128 | 0.25 | 16 | 0.03 | 16 |
| 29. Penicillium 1641 | 64 | 0.06 | 0.25 | 0.25 | 16 |
| 30. Penicillium 2548 | 128 | 0.03 | 0.25 | 0.125 | 16 |
| 31. Penicillium 3162 | >128 | 0.25 | 0.25 | 0.03 | 32 |
| 32. Penicillium 191 | 64 | 0.25 | 0.06 | 0.06 | 16 |
| 33. Penicilliuim 2306 | >128 | 0.25 | 0.125 | 0.016 | 8 |
| 34. Rhizopus 1052 | >128 | 0.06 | 16 | 0.0005 | 8 |
| 35. Rhizopus (Ceylon) | >128 | 64 | 64 | 0.125 | 2 |
| 36. Alternaria 1051 | >128 | 1 | 0.125 | 0.03 | 1 |
| 37. Fusarium 1050 | >128 | 0.5 | 64 | 1 | 64 |

TABLE 1-continued

Minimum Inhibitory Concentration (MIC) (μg/ml) of Standard drugs and compound of this invention against various fungi

| | Fluconazole | Amphotericin-B | Itraconazole | Compound No.1 (This invention) | TAK 187 |
|---|---|---|---|---|---|
| 38. Fusarium 2960C | >128 | 0.5 | 16 | 2 | 32 |
| 39. Fusarium 1827C | >128 | >128 | 128 | 2 | 32 |
| 40. Mucor (Ceylon) | >128 | 0.06 | 0.125 | 0.004 | 8 |

Prominent reduction in growth has been taken as MIC endpoint following National Committee for Clinical Laboratory Standard (NCCLS) M27A and M38 P
*Paecillomyces variotii* grows well in 48 h

TABLE 2

Minimum Fungicidal Concentration (MFC) (μg/ml) of Standard drugs and compounds of this invention against QC strains against various filamentous fungi

| | Fluconazole | Amphotericin-B | Itraconazole | Compound No.1 (This invention) | TAK 187 |
|---|---|---|---|---|---|
| 1. C krusei 6258 | 128 | 1 | 64 | 0.016 | 64 |
| 2. C parapsilosis 22019 | 4 | 32 | 8 | 0.016 | 0.03 |
| 3. P variotii 22319 | >128 | 2 | 0.06 | 0.06 | 32 |
| 4. A fumigatus SI-1 - 1019 | >128 | 2 | 0.25 | 0.03 | 32 |
| 5. A fumigatus 1008 | >128 | 1 | 0.06 | 0.03 | 8 |
| 6. A flavus P2 - 1045 | >128 | 1 | 0.25 | 0.03 | 32 |
| 7. A flavus P3 - 1041 | >128 | 0.5 | 0.06 | 0.06 | — |
| 8. A flavus E3 - 1044 | >128 | 0.5 | 0.03 | 0.03 | 8 |
| 9. A flavus E4 - 1042 | >128 | 0.125 | 0.125 | 0.03 | — |
| 10. A niger E5 - 1047 | >128 | 0.25 | 0.125 | 0.06 | 2 |
| 11. A niger P1 - 1046 | >128 | 0.25 | 0.25 | 0.06 | 0.5 |
| 12. Penicillium H - 1048 | >128 | 2 | >128 | 4 | >128 |
| 13. Penicillium I - 1049 | >128 | 4 | >128 | 1 | 128 |
| 14. Penicillium 1641 | >128 | 16 | 0.06 | 0.25 | 32 |
| 15. Penicillium 2548 | >128 | 4 | 0.06 | 0.125 | 16 |
| 16. Penicillium 31620 | >128 | 0.25 | 1 | 0.125 | 16 |
| 17. Penicillium 191 | >128 | 2 | 0.06 | 0.125 | 16 |
| 18. Penicillium 2306 | >128 | 0.5 | 16 | 0.06 | 16 |
| 19. Rhizopus 1052 | >128 | 8 | 8 | 0.03 | 32 |
| 20. Rhizopus (Ceylon) | >128 | 64 | 128 | 0.5 | >128 |
| 21. Alternaria 1051 | >128 | >128 | 32 | 0.06 | 16 |
| 22. Fusarium (Ceylon) | >128 | >128 | >128 | 32 | 128 |
| 23. Fusarium 29600 | >128 | >128 | >128 | >128 | >128 |
| 24. Fusarium 18270 | >128 | >128 | 128 | >128 | 32 |
| 25. Mucor (Ceylon) | >128 | 1 | >128 | 1 | >128 |

A comparative in vitro and in vivo biologically activity data of the compound of our invention, 2-{[1R,2R]-2-(2,4-Difluorophenyl)-2-hydroxy-1-methyl-3-(1H-1,2,4-triazole-1-yl)propyl}-4-[(2',2',3',3'-tetrafluoropropoxyphenyl)-3-(2H,4H)-1,2,4-thiotriazolone (Compound No. 3) with 2-[(1R,2R)-2-(2,4-difluorophenyl)-2-hydroxy-1-methyl-3-(1H-1,2,4-triazol-1-yl)propyl]-4-(2',2',3',3'-tetraflouropropoxyphenyl)-3(2H,4H)-1,2,4-triazolone (TAK 187) and standard antifungal pharmaceuticals is given below:

| | All fungal pathogens MIC (μg/ml) | | |
|---|---|---|---|
| | $MIC_{50}$ | $MIC_{90}$ | G.M. |
| Amphotericin B | 0.25 | 0.5 | 0.21 |
| Fluconazole | 256 | 256 | 105 |
| Itraconazole | 0.19 | 256 | 0.437 |
| TAK 187 | 8 | 32 | 4.16 |
| Compound No. 3 | 0.25 | 2 | 0.285 |

| | All Candida isolates MIC (μg/ml) | | |
|---|---|---|---|
| | $MIC_{50}$ | $MIC_{90}$ | G.M. |
| Amphotericin B | 0.25 | 0.25 | 0.22 |
| Fluconazole | 8 | 128 | 5.3 |
| Itraconazole | 0.25 | 0.5 | 0.1 |
| TAK 187 | 0.5 | 2 | 0.45 |
| Compound No. 3 | 0.5 | 1 | 0.1 |

| | All Filamentous isolates MIC (μg/ml) | | |
|---|---|---|---|
| | $MIC_{50}$ | $MIC_{90}$ | G.M. |
| Amphotericin B | 0.25 | 0.5 | 0.22 |
| Fluconazole | 256 | 256 | 199 |
| Itraconazole | 0.25 | 256 | 0.6 |

-continued

| TAK 187 | 8 | 32 | 7.246 |
|---|---|---|---|
| Compound No. 3 | 0.25 | 8 | 0.328 |

| *Aspergillus fumigatus* isolates MIC (μg/ml) | | | |
|---|---|---|---|
| | MIC$_{50}$ | MIC$_{90}$ | G.M. |
| Amphotericin B | 0.25 | 0.5 | 0.27 |
| Fluconazole | 256 | 256 | 256 |
| Itraconazole | 0.25 | 0.5 | 0.181 |
| TAK 187 | 8 | 8 | 7.4 |
| Compound No. 3 | 0.125 | 0.25 | 0.112 |

| Rhizoupus spp. isolates MIC (μg/ml) | | | |
|---|---|---|---|
| | MIC$_{50}$ | MIC$_{90}$ | G.M. |
| Amphotericin B | 0.125 | 0.25 | 0.177 |
| Fluconazole | 256 | 256 | 256 |
| Itraconazole | 16 | 64 | 32 |
| TAK 187 | 4 | 4 | 4 |
| Compound No. 3 | 0.125 | 0.125 | 0.125 |

| Fusarium spp. isolates MIC (μg/ml) | | | |
|---|---|---|---|
| | MIC$_{50}$ | MIC$_{90}$ | G.M. |
| Amphotericin B | 0.5 | 2 | 0.841 |
| Fluconazole | 256 | 256 | 256 |
| Itraconazole | 64 | 256 | 90.51 |
| TAK 187 | 32 | 64 | 45.255 |
| Compound No. 3 | 8 | 8 | 8 |

| Penicillium spp. isolates MIC (μg/ml) | | | |
|---|---|---|---|
| | MIC$_{50}$ | MIC$_{90}$ | G.M. |
| Amphotericin B | 0.25 | 0.25 | 0.144 |
| Fluconazole | 256 | 256 | 174.181 |
| Itraconazole | 0.5 | 256 | 0.922 |
| TAK 187 | 16 | 64 | 18.664 |
| Compound No. 3 | 2 | 8 | 1.516 |

| Activity against dermatophytes | | | | |
|---|---|---|---|---|
| Organism | Fluconazole | Itraconazole | Terbina | Compound No. 3 |
| *T. mentagrophyte* | >128 | 0.125 | 0.002 | 0.016 |
| *T. rubrum* | >128 | 0.03 | 0.016 | 0.004 |

In vivo Anti-fungal Activity of Compound No. 3; Determination of 50% Effective Dose (ED$_{50}$)

Method: Briefly, Swiss albino mice weighing 20±2 G were injected intravenously (tail vein) with sufficient fungal cells to kill 100% of the untreated animals for *Aspergillus fumigatous* strain used. In all cases each group comprised of six mice. Five does levels, utilizing doubling dilution range, were employed per determination ranging from 25 to 1.56 mg/kg BW. Dosing was carried out for five days starting after 30 minutes of infection. A mortality rate of 100% was observed in all groups of untreated mice. Treated animals were monitored twice daily for 14 days post infection at which time the experiment was terminated and ED$_{50}$ was calculated.

Results:

| | ED50 in mg/kg body weight | |
|---|---|---|
| Drug | Day 7 post infection | Day 14 post infection |
| Compound No. 3 | 2.33 | 6.25 |
| Itraconazole | 8.84 | 21.02 |
| TAK 187 | 10.08 | 20.39 |
| Infection control | — | — |

While the present invention has been described in terms of its specific embodiments, certain modifications and equivalents will be apparent to those skilled in the art and are intended to be included within the scope of the present invention.

We claim:

1. A compound of Formula I,

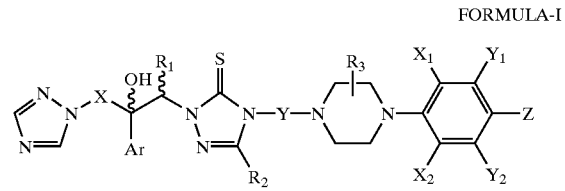

FORMULA-I and its pharmaceutically acceptable salts, enantiomers, diastereomers, or N-oxides, wherein X is selected from the group consisting of CH$_2$, CO, CS, and SO$_2$;

Ar is a substituted phenyl group having one to three substituents independently selected from a halogen, C$_1$–C$_4$ alkyl, halogenated lower (C$_1$–C$_4$) alkyl group and halogenated lower (C$_1$–C$_4$) alkoxy group;

R$_1$ and R$_2$ are each independently selected from the group consisting of hydrogen, C$_1$–C$_4$ alkyl, C$_1$–C$_4$ alkoxy, amino, hydroxy, nitro, cyano, carboxyl, and SO$_2$R' wherein R' is hydrogen, or alkyl;

Y is a phenyl group which is unsubstituted or substituted by 1–3 substituents each independently selected from the group consisting of halogen, nitro, amino, cyano, carboxyl, hydroxy, C$_1$–C$_4$ alkyl, C$_1$–C$_4$ alkoxy and SO$_2$R' wherein R' is hydrogen, or alkyl;

R$_3$ is selected from the group consisting of hydrogen, C$_1$–C$_4$ alkyl group, C$_1$–C$_4$ alkoxy, nitro, amino, cyano, carboxyl, and SO$_2$R' wherein R' is hydrogen, or alkyl, and X$_1$, X$_2$, Y$_1$, Y$_2$ and Z are independently selected from the group consisting of hydrogen, halogen, nitro, cyano, amino, aryl, C$_1$–C$_4$, alkyl, C$_1$–C$_4$ alkoxy, halogenated lower (C$_1$–C$_4$) alkyl group, halogenated lower (C$_1$–C$_4$) alkoxy group and carboxyl.

2. A compound of Formula II,

FORMULA-II

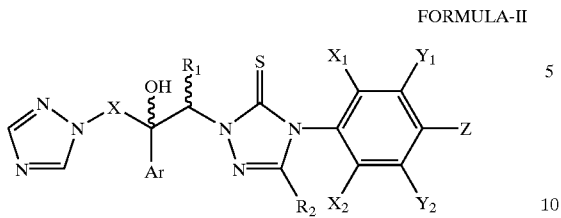

and its pharmaceutically acceptable salts, enantiomers, diastereomers, or N-oxides, wherein X is selected from the group consisting of $CH_2$, CO, CS, and $SO_2$;

Ar is a substituted phenyl group having one to three substituents independently selected from a halogen, $C_1$–$C_4$ alkyl, halogenated lower ($C_1$–$C_4$) alkyl group and halogenated lower ($C_1$–$C_4$) alkoxy group;

$R_1$ and $R_2$, are each independently selected from the group consisting of hydrogen, $C_1$–$C_4$ alkyl, $C_1$–$C_4$ alkoxy, amino, hydroxy, nitro, cyano, carboxyl, and $SO_2R'$ wherein R' is hydrogen, or alkyl; and $X_1$, $X_2$, $Y_1$, $Y_2$ and Z are independently selected from the group consisting of hydrogen halogen, nitro, cyano, amino, aryl, $C_1$–$C_4$, alkyl, $C_1$–$C_4$ alkoxy, halogenated lower ($C_1$–$C_4$) alkyl group, halogenated lower ($C_1$–$C_4$) alkoxy group and carboxyl.

3. A compound selected from the group consisting of:

2-{[1R,2R]-2-(2,4-difluorophenyl)-2-hydroxy-1-methyl-3-(1H-1,2,4-triazole-1-yl)propyl}-4-{4-[4-(4-chlorophenyl)-1-piperazinyl]phenyl}-3-(2H,4H)-1,2,4-thiotriazolone (Compound No. 1)

2-{[1R,2R]-2-(2,4-difluorophenyl)-2-hydroxy-1-methyl-3-(1H-1,2,4-trizole-1-yl)propyl}-1-[4-(4-methoxyphenyl)]-3-(2H,4H)-1,2,4-thiotriazolone (Compound No. 2) and 2-{[1R,2R]-2-(2,4-difluorophenyl)-2-hydroxy-1-methyl-3(1H-1,2,4-triazol-1-yl)propyl}-4-(2',2',3',3'-tetrafluropropoxy-phenyl)-3-(2H,4H)-1,2,4-thiotriazolone (Compound No. 3).

4. A pharmaceutical composition comprising the compound of claims 1, 2 or 3 and a pharmaceutical acceptable carrier.

5. A pharmaceutical composition comprising a pharmaceutically effective amount of compound according to claims 1, 2 or 3 or a physiologically acceptable acid additional salt thereof with a pharmaceutically acceptable carrier.

6. A method of treating or preventing fungal infection in mammals comprising administering to said mammal a compound of Formula I

FORMULA-I

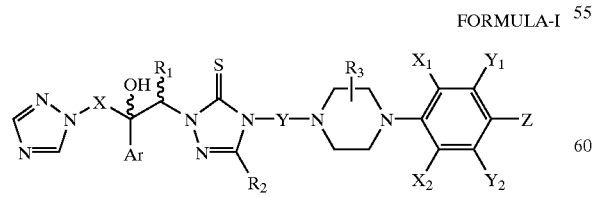

and its pharmaceutically acceptable salts, enantiomers, diastereomers, or N-oxides, wherein X is selected from the group consisting of $CH_2$, CO, CS, and $SO_2$;

Ar is a substituted phenyl group having one to three substituents independently selected from a halogen, $C_1$–$C_4$ alkyl, halogenated lower ($C_1$–$C_4$) alkyl group and halogenated lower ($C_1$–$C_4$) alkoxy group;

$R_1$ and $R_2$ are each independently selected from the group consisting of hydrogen, $C_1$–$C_4$ alkyl, $C_1$–$C_4$ alkoxy, amino, hydroxy, nitro, cyano, carboxyl, and $SO_2R'$ wherein R' is hydrogen, or alkyl;

Y is a phenyl group which is unsubstituted or substituted by 1–3 substituents each independently selected from the group consisting of halogen, nitro, amino, cyano, carboxyl, hydroxy, $C_1$–$C_4$ alkyl, $C_1$–$C_4$ alkoxy and $SO_2R'$ wherein R' is hydrogen, or alkyl;

$R_3$ is selected from the group consisting of hydrogen, $C_{1-C4}$ alkyl group, $C_1$–$C_4$ alkoxy, nitro, amino, cyano, carboxyl, and $SO_2R'$ wherein R' is hydrogen, or alkyl; and $X_1$, $X_2$, $Y_1$, $Y_2$ and Z are independently selected from the group consisting of hydrogen halogen, nitro, cyano, amino, aryl, $C_1$–$C_4$, alkyl, $C_1$–$C_4$ alkoxy, halogenated lower ($C_1$–$C_4$) alkyl group, halogenated lower ($C_1$–$C_4$) alkoxy group and carboxyl.

7. A method of treating or preventing fungal infection in mammals comprising administering to said mammal a compound of Formula II

FORMULA-II

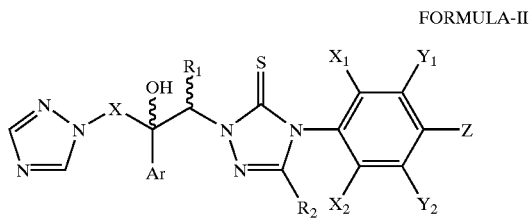

and its pharmaceutically acceptable salts, enantiomers, diastereomers, or N-oxides, wherein X is selected from the group consisting of $CH_2$, CO, CS, and $SO_2$;

Ar is a substituted phenyl group having one to three substituents independently selected from a halogen $C_1$–$C_4$ alkyl, halogenated lower ($C_1$–$C_4$) alkyl group and halogenated lower ($C_1$–$C_4$) alkoxy group;

$R_1$ and $R_2$ are each independently selected from the group consisting of hydrogen, $C_1$–$C_4$ alkyl, $C_1$–$C_4$ alkoxy, amino, hydroxy, nitro, cyano, carboxyl, and $SO_2R'$ wherein R' is hydrogen, or alkyl; and $X_1$, $X_2$, $Y_1$, $Y_2$ and Z are independently selected from the group consisting of hydrogen halogen, nitro, cyano, amino, aryl, $C_1$–$C_4$, alkyl, $C_1$–$C_4$ alkoxy, halogenated lower ($C_1$–$C_4$) alkyl group, halogenated lower ($C_1$–$C_4$) alkoxy group and carboxyl.

8. A process for preparing a compound of Formula I

FORMULA-I

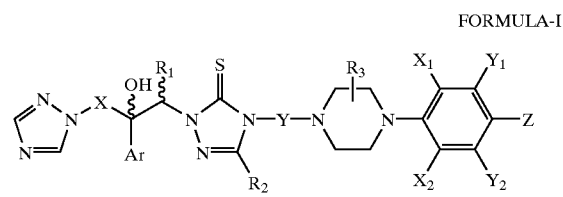

and its pharmaceutically acceptable salts, enantiomers, diastercomers, or N-oxides, wherein X is selected from the group consisting of $CH_2$, CO, CS, and $SO_2$;

Ar is a substituted phenyl group having one to three substituents independently selected from a halogen, $C_1$–$C_4$ alkyl, halogenated lower ($C_1$–$C_4$) alkyl group and halogenated lower ($C_1$–$C_4$) alkoxy group;

$R_1$ and $R_2$ are each independently selected from the group consisting of hydrogen, $C_1$–$C_4$ alkyl, $C_1$–$C_4$ alkoxy, amino, hydroxy, nitro, cyano, carboxyl, and $SO_2R'$ wherein R' is hydrogen, or alkyl;

Y is a phenyl group which is unsubstituted or substituted by 1–3 substituents each independently selected from the group consisting of halogen, nitro, amino, cyano, carboxyl, protected carboxyl, hydroxy, $C_1$–$C_4$ alkyl, $C_1$–$C_4$ alkoxy and $SO_2R'$ wherein R' is hydrogen, or alkyl;

$R_3$ is selected from the group consisting of hydrogen, $C_1$–$C_4$ alkyl group, $C_1$–$C_4$ alkoxy, nitro, amino, cyano, carboxyl, protected caboxyl and $SO_2R'$ wherein R' is hydrogen, or alkyl; and $X_1$, $X_2$, $Y_1$, $Y_2$ and Z are independently selected from the group consisting of hydrogen halogen, nitro, cyano, amino, aryl, $C_1$–$C_4$, alkyl, $C_1$–$C_4$ alkoxy, halogenated lower ($C_1$–$C_4$) alkyl group, halogenated lower ($C_1$–$C_4$) alkoxy group and carboxyl;

which comprises reacting the compound of Formula III,

FORMULA-III

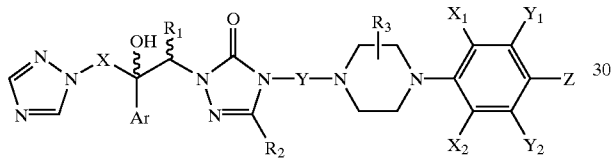

wherein X, Ar, $R_1$, $R_2$, Y, $R_3$, $X_1$, $X_2$, $Y_1$, $Y_2$ and Z have the same meanings, as defined above, with modified Lawesson's reagent of Formula V

FORMULA V

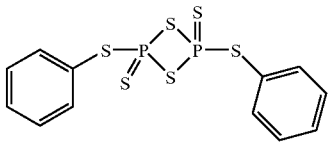

MODIFIED LAWESSON'S REAGENT to afford the compound of Formula I.

9. A process for preparing a compound of Formula II

FORMULA-II

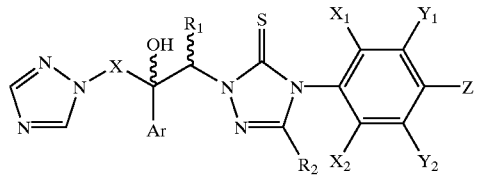

and its pharmaceutically acceptable salts, enantiomers, diastereomers, or N-oxides, wherein X is selected from the group consisting of $CH_2$, CO, CS, and $SO_2$;

Ar is a substituted phenyl group having one to three substituents independently selected from a halogen $C_1$–$C_4$ alkyl, halogenated lower ($C_1$–$C_4$) alkyl group and halogenated lower ($C_1$–$C_4$) alkoxy group;

$R_1$ and $R_2$ are each independently selected from the group consisting of hydrogen, $C_1$–$C_4$ alkyl, $C_1$–$C_4$ alkoxy, amino, hydroxy, nitrocyano, carboxyl, and $SO_2R'$ wherein R' is hydrogen, or alkyl; and $X_1$, $X_2$, $Y_1$, $Y_2$ and Z are independently selected from the group consisting of hydrogen halogen, nitro, cyano, amino, aryl, $C_1$–$C_4$, alkyl, $C_1$–$C_4$ alkoxy, halogenated lower ($C_1$–$C_4$) alkyl group, halogenated lower ($C_1$–$C_4$) alkoxy group and carboxyl;

which comprises reacting the compound of Formula IV

FORMULA-III

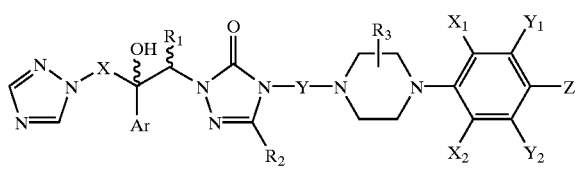

wherein X, Ar, $R_1$, $R_2$, $X_1$, $X_2$, $Y_1$, $Y_2$ and Z are the same as defined above, with modified Lawesson's reagent or Formula V

FORMULA V

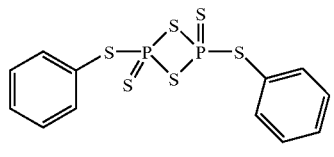

MODIFIED LAWESSON'S REAGENT to afford the compound of Formula II.

10. A process for preparing a compound namely 2-[(1R,2R)-2-(2,4-difluorophenyl)-2-hydroxy-1-methyl-3-(1H-1,2,4-triazol-1-yl)propyl]-4-(2',2',3',3'-tetrafluoropropoxyphenyl)-3-(2H,4H)-1,2,4-thiotriazolone and its pharmaceutically acceptable salts, enantiomers, diastereomers, or N-oxides, which comprises reacting 2-[(1R,2R)-2-(2,4-difluorophenyl)-2-hydroxy-1-methyl-3-(1H-1,2,4-triazol-1-yl)propyl]-4-(2',2',3',3'-tetrafluoropropoxyphenyl)-3(2H,4H)-1,2,4-triazolone with Lawesson's reagent.

* * * * *

UNITED STATES PATENT AND TRADEMARK OFFICE
CERTIFICATE OF CORRECTION

PATENT NO. : 6,710,049 B2
DATED : March 23, 2004
INVENTOR(S) : Salman et al.

It is certified that error appears in the above-identified patent and that said Letters Patent is hereby corrected as shown below:

<u>Title page,</u>
Item [57], ABSTRACT,
Line 4, after the first sentence insert the following: -- More particularly, the compounds are of the class of, for example, 2-aryl-2-hydroxy 1-triazolyl-3-thiotriazolyl propanes and derivatives thereof. --

<u>Column 1,</u>
Line 1, "in-vivo" should be italicized
Line 28, "zygomiycetes" should read -- zygomycetes -- (should be italicized too)
Lines 29 & 30 and 47, "non-albicans candidia" should be italicized
Line 56, "Rhizopus" should be italicized
Lines 58 and 59, "Mucor, Rhizomucor, and Absidia" should be italicized
Line 59, "Zygomycetes" should be italicized
Line 63, "Fusarium" should be italicized <u>Column 2,</u>
Lines 14 and 50, "in-vitro" should be italicized
Line 38, "Clortrimazole" should read -- Clotrimazole --
Line 51, "in-vivo" should be italicized <u>Column 3,</u>
Line 7, "aspergillosis" should be italicizied
Lines 22 (both occurrences) and 24 (both occurrences), "in-vitro" should be italicized
Line 34, "Confernece" should read -- Conference --
Line 58, "pharamcokinetic" should read -- pharmacokinetic --

<u>Column 4,</u>
Lines 13 and 67, "metabolities" should read -- metabolites --
Line 32, "4-chlopheny)" should read -- 4-chlorophenyl --

<u>Column 5,</u>
Line 42, "in-vivo" should be italicized

<u>Column 7,</u>
Line 13, "Yokohamna et al. in Synthesis," should read -- Yokoyama et al. in Communications --
Line 46, "diastereomers" should read -- diastereomers, --
Line 47 "metabolities" should read -- metabolites --

UNITED STATES PATENT AND TRADEMARK OFFICE
CERTIFICATE OF CORRECTION

PATENT NO. : 6,710,049 B2
DATED : March 23, 2004
INVENTOR(S) : Salman et al.

It is certified that error appears in the above-identified patent and that said Letters Patent is hereby corrected as shown below:

Column 8,
Line 13 & 14, "Yokohama et at in Synthesis" should read -- Yokoyama et al. in Communications --
Lines 27 and 31, "{[1R2R]" should read -- {[1R,2R] --
Lines 59 and 62, "in-vacuo" should be italicized Column 10,
Line 43, "Fusarium" should be italicized
Line 43, "Rhizopus" should be italicized
Line 49, "in-vitro" should be italicized Column 13,
Line 54, "tetratlouropropoxyphenyl" should read -- tetrafluoropropoxyphenyl --

Columns 13 & 14,
Table 2, #16, "Penicillium 31620" should read -- Penicillium 3162C --
Table 2, #23, "Fusarium 29600" should read -- Fusarium 2960C --
Table 2, #24, "Fusarium 18270" should read -- Fusarium 1827C --

Column 15,
Line 59, "does" should read -- dose --

Column 17,
Line 26, "hydrogen halogen" should read -- hydrogen, halogen --
Line 27, "amino, aryl" should read -- amino, sulphonyl, aryl --

Column 18,
Lines 18 and 49, "hydrogen halogen" should read -- hydrogen, halogen --
Lines 19 and 50, "amino, aryl" should read -- amino, sulphonyl, aryl --

Column 19,
Line 20, "hydrogen halogen" should read -- hydrogen, halogen --
Line 21, "amino, aryl" should read -- amino, sulphonyl, aryl --

UNITED STATES PATENT AND TRADEMARK OFFICE
CERTIFICATE OF CORRECTION

PATENT NO. : 6,710,049 B2
DATED : March 23, 2004
INVENTOR(S) : Salman et al.

It is certified that error appears in the above-identified patent and that said Letters Patent is hereby corrected as shown below:

Column 20,
Line 10, "nitrocyano" should read -- nitro, cyano --
Line 14, "hydrogen halogen" should read -- hydrogen, halogen --
Line 22, "Formula III" should read -- Formula IV --
Line 33, "or" should read -- of --
Line 51, "diflurophenyl" should read -- difluorophenyl --

Signed and Sealed this

Twenty-first Day of December, 2004

JON W. DUDAS
*Director of the United States Patent and Trademark Office*